(12) United States Patent
Bian et al.

(10) Patent No.: US 9,895,515 B2
(45) Date of Patent: Feb. 20, 2018

(54) PERFUSION CATHETER SYSTEM FOR SIMULTANEOUS DELIVERY OF CARDIOPLEGIA TO THE LEFT AND RIGHT CORONARY ARTERY

(71) Applicants: Xiaoming Bian, Dalian (CN); Frank Zheng, Kirkland, WA (US)

(72) Inventors: Xiaoming Bian, Dalian (CN); Frank Zheng, Kirkland, WA (US)

(73) Assignee: Corvivo Inc., Coquitlam, BC (CA)

( * ) Notice: Subject to any disclaimer, the term of this patent is extended or adjusted under 35 U.S.C. 154(b) by 33 days.

(21) Appl. No.: 13/843,795

(22) Filed: Mar. 15, 2013

(65) Prior Publication Data

US 2014/0276399 A1    Sep. 18, 2014

(51) Int. Cl.
*A61M 25/10* (2013.01)
*A61M 25/00* (2006.01)

(52) U.S. Cl.
CPC .......... *A61M 25/10* (2013.01); *A61M 25/007* (2013.01); *A61M 25/0071* (2013.01); *A61M 25/0074* (2013.01); *A61M 25/1011* (2013.01); *A61M 2025/1045* (2013.01); *A61M 2025/1052* (2013.01)

(58) Field of Classification Search
CPC .. A61M 25/10; A61M 25/0041; A61M 25/04; A61M 2025/0177; A61M 2025/024; A61M 2025/0213; A61M 2025/0233; A61M 2025/1045; A61M 2025/1047; A61M 25/104; A61M 25/008; A61M 25/0071; A61F 2/247; A61F 2/2433; A61F 2/2403; A61F 2/2409

USPC .......................................................... 604/43
See application file for complete search history.

(56) References Cited

U.S. PATENT DOCUMENTS

| | | | |
|---|---|---|---|
| 5,197,952 A | 3/1993 | Marcadis et al. | |
| 5,476,453 A | 12/1995 | Mehta | |
| 5,505,698 A | 4/1996 | Booth et al. | |
| 5,695,457 A | 12/1997 | St. Goar et al. | |
| 6,554,802 B1 * | 4/2003 | Pearson | A61M 25/02 604/165.03 |
| 6,913,601 B2 | 7/2005 | St. Goar et al. | |
| 2004/0111104 A1 * | 6/2004 | Schein | A61B 17/00 606/153 |
| 2005/0033361 A1 * | 2/2005 | Galdonik | A61B 17/0057 606/213 |

(Continued)

FOREIGN PATENT DOCUMENTS

EP         0 745 406 A2    12/1996

*Primary Examiner* — Nathan R Price
*Assistant Examiner* — Melissa A Snyder
(74) *Attorney, Agent, or Firm* — Inskeep IP Group, Inc.

(57) ABSTRACT

A perfusion catheter system comprises a main line, a first branch line having a tip at a distal end thereof, and a second branch line having a tip at a distal end thereof. The tip of the first branch line is heavier than the tip of the second branch line. The tip of the first branch line may be weighted. There may be a self-inflating balloon at the tip of the first branch line. There may be a self-inflating balloon at the tip of the second branch line. There may be a clamp disposed along the second branch line. The clamp may include a base, a clamping arm hingedly connected to the base, and an aperture extending through the base. The second branch line may extend through the aperture in the base.

4 Claims, 2 Drawing Sheets

(56) References Cited

U.S. PATENT DOCUMENTS

2005/0209581 A1* 9/2005 Butts et al. .................. 604/523
2010/0204765 A1* 8/2010 Hall et al. .................... 607/105

* cited by examiner

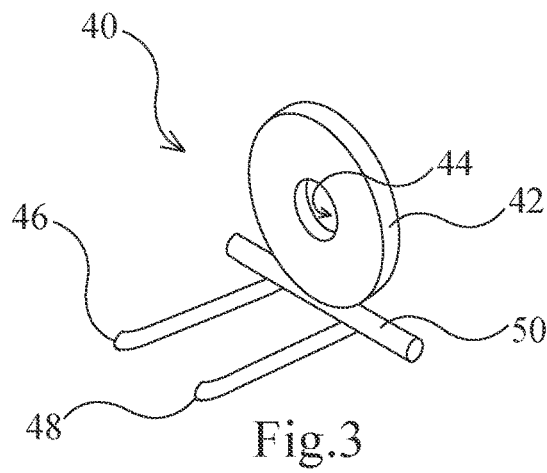
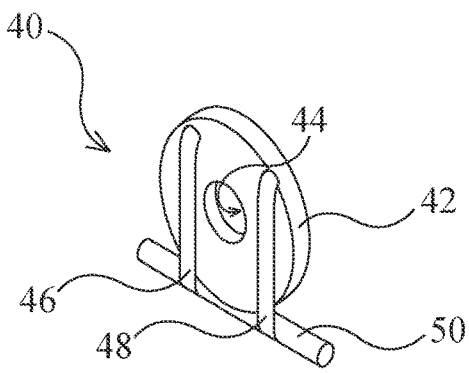
Fig.3  Fig.4
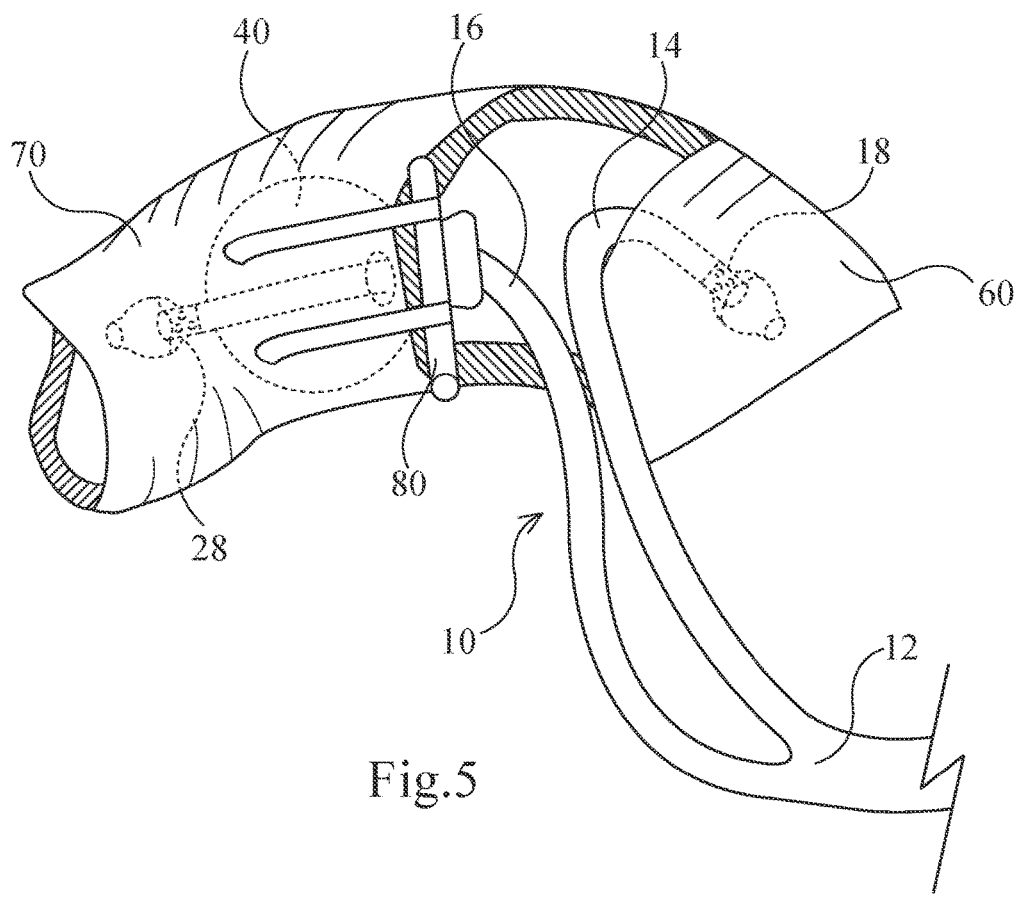
Fig.5

PERFUSION CATHETER SYSTEM FOR SIMULTANEOUS DELIVERY OF CARDIOPLEGIA TO THE LEFT AND RIGHT CORONARY ARTERY

BACKGROUND OF THE INVENTION

Field of the Invention

The present invention relates to catheters and, in particular, to a perfusion catheter system for simultaneous delivery of cardioplegia to the ostium of both the left and right coronary artery.

Description of the Related Art

It is often necessary to deliver cardioplegia to both the left and right ostium coronary artery during aortic surgery. Conventionally, separate hand-held left and right coronary artery perfusion catheters are used. The left and right coronary artery perfusion catheters have different orientations at their distal ends to correspond with the respective orientations of the left and right coronary ostiums. It is however also known to use a single perfusion catheter system to deliver cardioplegia to the ostium of both the left and right coronary artery. For example, U.S. Pat. No. 5,695,457 which issued on Dec. 9, 1997 to St. Goar et al. discloses a perfusion catheter system which includes a first distal branch for engaging the left coronary ostium and a second distal branch for engaging the right coronary ostium. The catheter system may further include a third distal branch for venting blood from the left ventricle of the heart.

SUMMARY OF THE INVENTION

There is accordingly provided a perfusion catheter system comprising a main line, a first branch line having a tip at a distal end thereof, and a second branch line having a tip at a distal end thereof. The tip of the first branch line is heavier than the tip of the second branch line. The tip of the first branch line may be weighted. There may be a self-inflating balloon at the tip of the first branch line. There may be a self-inflating balloon at the tip of the second branch line. There may be a clamp disposed along the second branch line. The clamp may include a base, a clamping arm hingedly connected to the base, and an aperture extending through the base. The second branch line may extend through the aperture in the base.

BRIEF DESCRIPTION OF THE DRAWINGS

The invention will be more readily understood from the following description of the embodiments thereof given, by way of example only, with reference to the accompanying drawings, in which:

FIG. 3 is a perspective view of the clamp shown in FIG. 2 in an open configuration;

FIG. 4 is a perspective view of the clamp shown in FIG. 1 in a clamping configuration; and FIG. 5 is a fragmentary, perspective view of the perfusion catheter system and the clamp shown in FIG. 2 used to simultaneously deliver cardioplegia to the left and right coronary ostiums.

DESCRIPTION OF THE PREFERRED EMBODIMENTS

Figure 1:
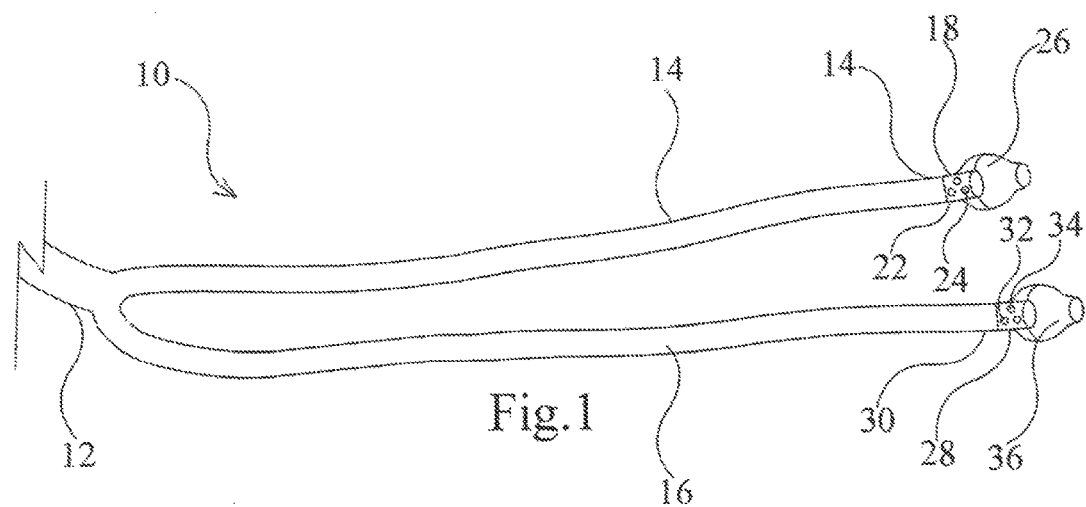
FIG. 1 is a fragmentary, perspective view of an improved perfusion catheter system.

Referring to the drawings and first to FIG. 1, an improved perfusion catheter system 10 is shown. The perfusion catheter system 10 generally comprises a main line 12, which is shown in fragment, a first branch line 14, and a second branch line 16. The first branch line 14 has a tip 18 at a distal end 20 thereof. There is a plurality of apertures, for example apertures 22 and 24, at the tip 18 of the first branch line 14. The apertures 22 and 24 allow for fluid communication between the first branch line 14 and the surrounding environment for continuous perfusion. There is also a self-inflating balloon 26 at the tip 18 of the first branch line 14. The self-inflating balloon 26 prevents leakage when the first branch line 14 is in use. Likewise the second branch line 16 has a tip 28 at a distal end 30 thereof. There is a plurality of apertures, for example apertures 32 and 34, at the tip 28 of the second branch line 16. The apertures 32 and 34 allow for fluid communication between the second branch line 16 and the surrounding environment for continuous perfusion. There is also a self-inflating balloon 36 at the tip 28 of the second branch line 16. The self-inflating balloon 26 prevents leakage when the second branch line 16 is in use.

The first branch line 14 and the second branch line 16 are both flexible in this example and, as thus far described, substantially similar. However, the first branch line 14 and the second branch line 16 differ in that the tip 18 of the first branch line 14 is made of weighted material such as metal, or is loaded with a weight, while the tip 28 of the second branch line 16 is made of a light material such as plastic. The tip 18 of the first branch line 14 is accordingly heavier than the tip 28 of the second branch line 16. The weighted tip 18 of the first branch line 14 facilitates engagement with the left coronary ostium because the weighted tip 18 of the first branch line gravitates to the left coronary ostium. The first branch line 14 may accordingly be used as a left coronary artery perfusion catheter line while the second branch line 16 may be used as a right coronary artery perfusion catheter line.

Figure 2:
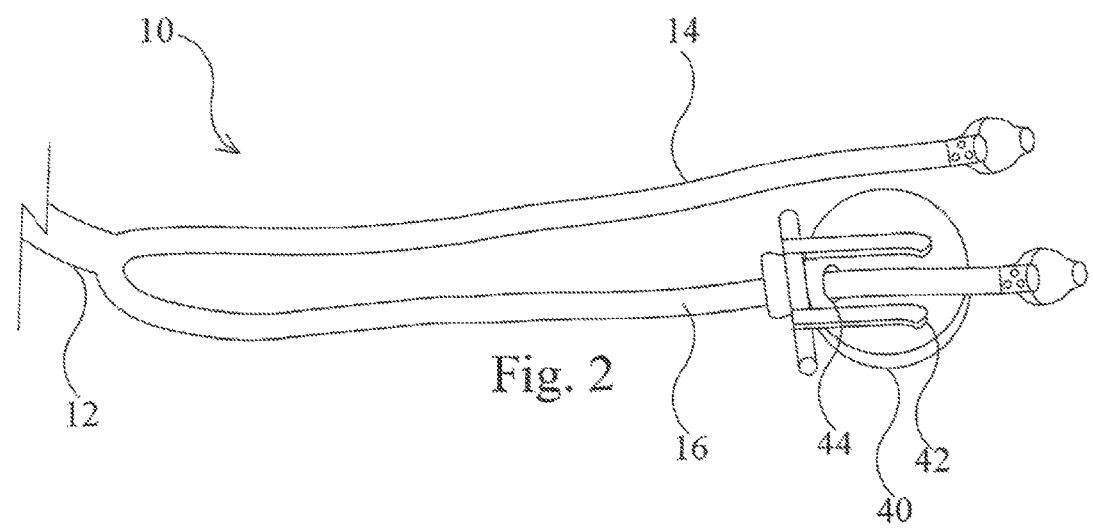
FIG. 2 is another fragmentary, perspective view of the improved perfusion catheter system shown in FIG. 1 further provided with a clamp.

The perfusion catheter system 10 is further provided with a clamp 40, shown in FIG. 2, which facilitates engagement of the second branch line 16 with the right coronary ostium. The clamp 40 is disposed along the second branch line 16 and is shown in greater detail in FIGS. 3 and 4. The clamp 40 includes a base 42 which, in this example, is annular and is made of Dacron®. There is an aperture 44 in the base 42 of the clamp 40 through which the second branch line 16 extends as shown in FIG. 2. Referring back to FIGS. 3 and 4, the clamp also includes clamping arms 46 and 48 which extend from a hinge 50. FIG. 3 shows the clamp 40 in an open configuration in which the clamping arms 46 and 48 are rotated away from the base 42 and FIG. 4 shows the clamp 40 in a clamping configuration in which the clamping arms 46 and 48 are rotated to a position where they are adjacent to the base.

FIG. 5 shows the perfusion catheter system 10 used as a perfusion catheter system for simultaneous delivery of cardioplegia to the ostium of both the left and right coronary arteries. The first branch line 14 or left coronary artery perfusion catheter line engages the left coronary ostium 60 while the second branch line 16 or right coronary artery perfusion catheter line engages the right coronary ostium 70. The weighted tip 18 of the first branch line 14 generally remains stationary in the left coronary ostium 60. The clamp 40 slides up against the aortic wall 80 and clamps to the aortic wall to anchor the tip 28 of the second branch line 16 in the right coronary ostium 70.

It will be understood by a person skilled in the art that although the perfusion catheter system disclosed herein is described for use in the simultaneous delivery of cardioplegia to the ostium of both the left and right coronary arteries that the suction tube may be used in other applications.

It will be understood by a person skilled in the art that many of the details provided above are by way of example only, and are not intended to limit the scope of the invention which is to be determined with reference to the following claims.

What is claimed is:

1. A perfusion catheter system for simultaneous delivery of cardioplegia to a left coronary ostium and a right coronary ostium, the perfusion catheter system comprising:
   a main line;
   a first branch line which is a left coronary artery perfusion catheter line having a tip at a distal end thereof;
   a second branch line which is a right coronary artery perfusion catheter line having a tip at a distal end thereof; and
   a clamp disposed along the second branch line, the clamp including a base with an aperture extending through the base and clamping arm hingedly connected to the base;
   wherein the tip of the first branch line is heavier than the tip of the second branch line so that the first branch line gravitates to the left coronary ostium during the delivery of cardioplegia and wherein the second branch line extends through the aperture in the base so that the clamp slides and clamps an aortic wall between the clamping arm and the base of the clamp to anchor the second branch line in the right coronary ostium during the delivery of cardioplegia.

2. The perfusion catheter system as claimed in claim 1 wherein the tip of the first branch line is weighted.

3. The perfusion catheter system as claimed in claim 1 further including a self-inflating balloon at the tip of the first branch line.

4. The perfusion catheter system as claimed in claim 1 further including a self-inflating balloon at the tip of the second branch line.

\* \* \* \* \*